United States Patent [19]
Marshall

[11] Patent Number: 5,109,873
[45] Date of Patent: May 5, 1992

[54] SURGICAL DRAPE

[75] Inventor: Lyman R. Marshall, Asheville, N.C.

[73] Assignee: Scherer Healthcare Ltd., Asheville, N.C.

[21] Appl. No.: 733,083

[22] Filed: Jul. 19, 1991

[51] Int. Cl.⁵ .................. A61B 19/00; A61B 19/08
[52] U.S. Cl. .................................. 128/849; 128/853
[58] Field of Search ............................ 128/849-856

[56] References Cited

U.S. PATENT DOCUMENTS

| | | | |
|---|---|---|---|
| 3,030,957 | 4/1962 | Melges | 128/856 |
| 3,154,789 | 11/1964 | Lewis, Jr. | 128/854 |
| 3,750,664 | 8/1973 | Collins | 128/853 |
| 3,797,484 | 3/1974 | Ericson | 128/853 |
| 3,862,632 | 1/1975 | Hinsch | 128/856 |
| 3,871,369 | 3/1975 | Krzewinski | 128/853 |
| 4,479,492 | 10/1984 | Singer | 128/853 |
| 4,869,271 | 9/1989 | Idris | 128/853 |
| 4,957,120 | 9/1990 | Grier-Idris | 128/853 |

*Primary Examiner*—Robert A. Hafer
*Assistant Examiner*—Michael Brown
*Attorney, Agent, or Firm*—David M. Carter

[57] ABSTRACT

There is provided an improved surgical drape in the form of a sheet having a fenestration therein through which a surgical procedure is performed. A score line is provided partially through the sheet from one outer edge thereof to the fenestration. The score line does not affect the sheet's capability of providing a sterile field. In procedures where a tube must remain in the site of the surgical procedure, the sheet may be easily severed along the score line by abruptly pulling the sides of the sheet separated by the score line. Thus the sheet may be removed from the patient without the need to cut the sheet with scissors.

14 Claims, 2 Drawing Sheets

SURGICAL DRAPE

BACKGROUND OF THE INVENTION

This invention relates to surgical drapes. More particularly it relates to surgical drapes having a fenestration or opening therein through which a surgical procedure is to be performed where such procedure requires that a tube or other elongated apparatus be left in the site of the procedure after completion thereof.

Surgical drapes are used during surgical procedures to provide a sterile field about the site of the procedure. In addition, the drape prevents blood and other bodily fluids from coming into contact with the patient as well as being spilled onto the operating room floor. Often the surgical drape has an opening therein near its center through which the procedure is performed. An adhesive may be applied around the opening with release paper covering the adhesive. When the drape is ready to be used, the release paper is removed and the adhesive is pressed against the body of the patient in the vicinity of the site of the procedure so that the drape will more readily remain in position.

There are many procedures which require tubes or other elongated apparatus, such as wires, to be placed into the site of the procedure and to remain in the site of the procedure for some time after closure. Because the tubes are received through the hole in the drape, it has been a problem to remove the drape after the procedure has been completed. Often scissors are used to cut the drape from one edge to the opening therein. Obviously the use of scissors near the site of the procedure and near other parts of the patient creates risk and furthermore it is awkward and often messy.

Surgical drapes have been provided which utilize perforations from one edge of the drape to the opening to aid in the removal of the drape from the patient. An example of such a drape is shown in FIGS. 1 and 2. For simplification, FIG. 1 only shows a portion of drape 10. Drape 10 has opening 12 therein through which a surgical procedure is to be performed and also has several in-line perforations 14. FIG. 2, which is a cross section of drape 10 taken through section line A—A, shows that perforations 14 extend all the way through drape 10. The perforations 14 are used to provide a weakened line so that the drape may be pulled apart by hand without the need for scissors. Since the perforations 14 pass completely through the drape, the reliability of the drape as a sterile field is reduced because microorganisms may readily pass through the perforations.

OBJECTS OF THE INVENTION

It is therefore one object of this invention to provide an improved surgical drape.

It is another object to provide a surgical drape which may be readily severed without the need for cutting apparatus while providing a reliable sterile field.

It is another object to provide a surgical drape which is easy to remove from the patient.

It is another object to provide a surgical drape which is easy and inexpensive to manufacture.

SUMMARY OF THE INVENTION

In accordance with one form of this invention, there is provided an improved surgical drape including a sheet of a material which is substantially impervious to microorganisms. The sheet has an opening therein through which a surgical procedure is to be performed. The sheet is adapted to be placed over a portion of a patient during the surgical procedure for providing a substantially sterile field. At least one score line is provided in the sheet between one edge of the sheet and the opening. Thus the sheet may be readily severed along the score line after completion of the procedure. This is particularly important when a tube or other elongated apparatus, such as wires, are left in the site of the procedure after the completion thereof so that the drape may be removed from the patient without the need to use a cutting instrument and without reducing the reliability of the sterile field.

In the preferred embodiment, the score line is in the form of an elongated notch which extends into the sheet to a depth of at least 35 percent of the total thickness of the sheet.

Also, preferably an adhesive is provided about the opening in the sheet to secure it to the patient. The adhesive should be slit where it is adjacent to the score line.

BRIEF DESCRIPTION OF THE DRAWINGS

The subject matter which is regarded as the invention is set forth in the appended claims. The invention itself however together with further objects and advantages thereof may be better understood with reference to the following description taken in conjunction with the accompanying drawings in which:

DESCRIPTION OF THE PREFERRED EMBODIMENT

Figure 1:
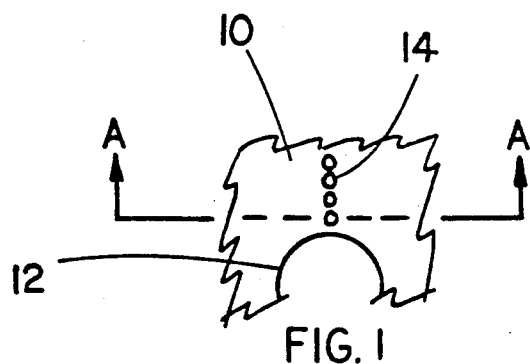
FIG. 1 is a partial plan view showing portions of a prior art surgical drape.

Referring now more particularly to FIGS. 3 through 6, there is provided surgical drape 16 including sheet 18 having opening or fenestration 20 therein. Sheet 18 is preferably made of a plastic material such as polyethylene having a thickness between 0.002 inch and 0.003 inch. Sheet 18 is substantially impermeable to microorganisms thereby presenting a substantially sterile field during a surgical procedure. Sheet 18 includes a pair of score lines 22 and 24. Score line 22 runs from edge 26 of sheet 18 to edge 28 of opening 20. Score line 24 runs from edge 30 of sheet 18 also to edge 28 of opening 20.

Figure 2:
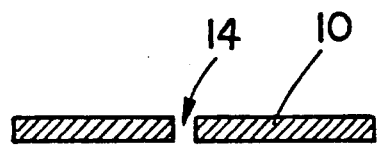
FIG. 2 is a sectional view of the drape of FIG. 1 taken through section lines A—A.
Figure 3:
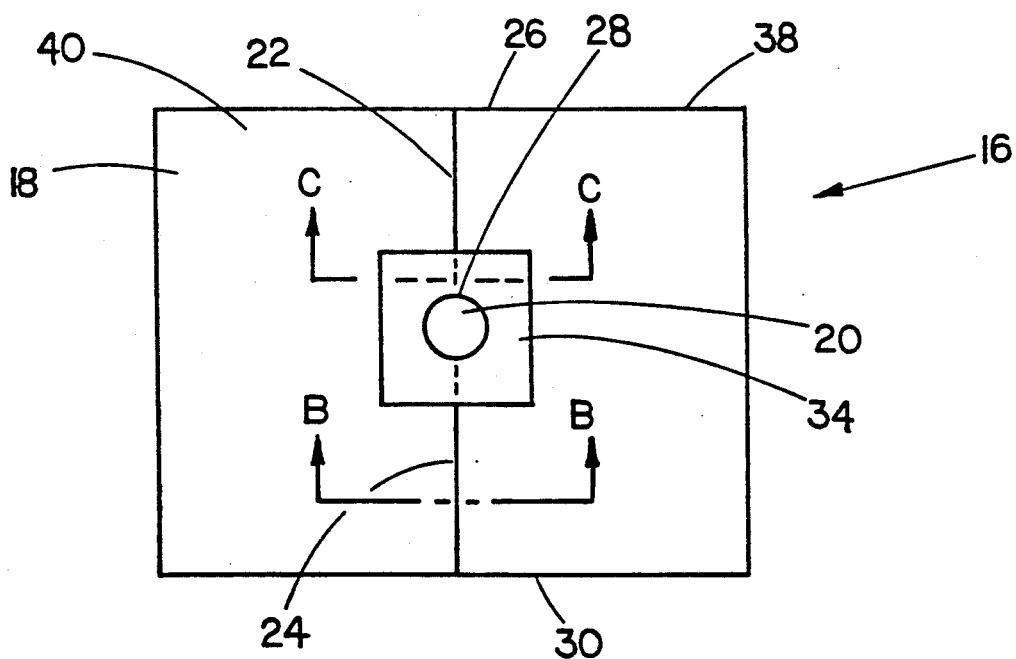
FIG. 3 is a plan view of the surgical drape of the subject invention.
Figure 4:
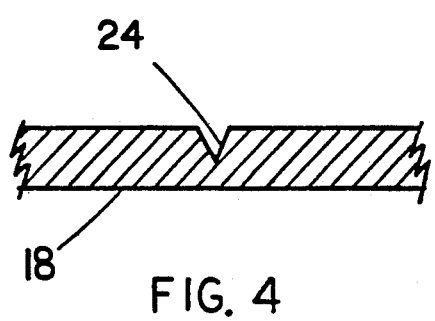
FIG. 4 is a sectional view of the drape of FIG. 3 taken through section lines B—B.
Figure 5:
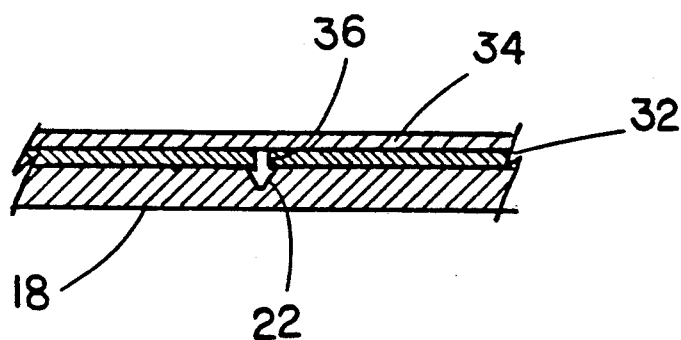
FIG. 5 is a sectional view of the surgical drape of FIG. 3 taken through lines C—C.

As can be seen from FIG. 4, the score lines of the preferred embodiment are V shaped and penetrate into a portion of drape 18. Preferably the score line extends to a depth of between 35% and 50% of the total thickness of drape 18. Drape 16 includes a layer of adhesive 32 which, in the preferred embodiment, is in the form of double sided tape. Adhesive 32 is completely covered by release paper 34. Adhesive 32 is slit completely through as indicated by opening 36. The slit in the adhesive as well as the score line in the sheet 18 are indicated by the dotted lines FIG. 3. By having score lines 22 and 24 only partially penetrating into sheet 18, the integrity of the sterile field created by sheet 18 is preserved as opposed to the prior art perforations which extend all the way through the sheet as shown in FIGS. 1 and 2. However, the score lines are deep enough to enable one to easily sever the sheet along one or both of the score lines by pulling or snapping the two halves 38 and 40 of sheet 18 in directions opposite to one another, resulting in the sheet being separated along the score line as shown in FIG. 6.

Figure 6:
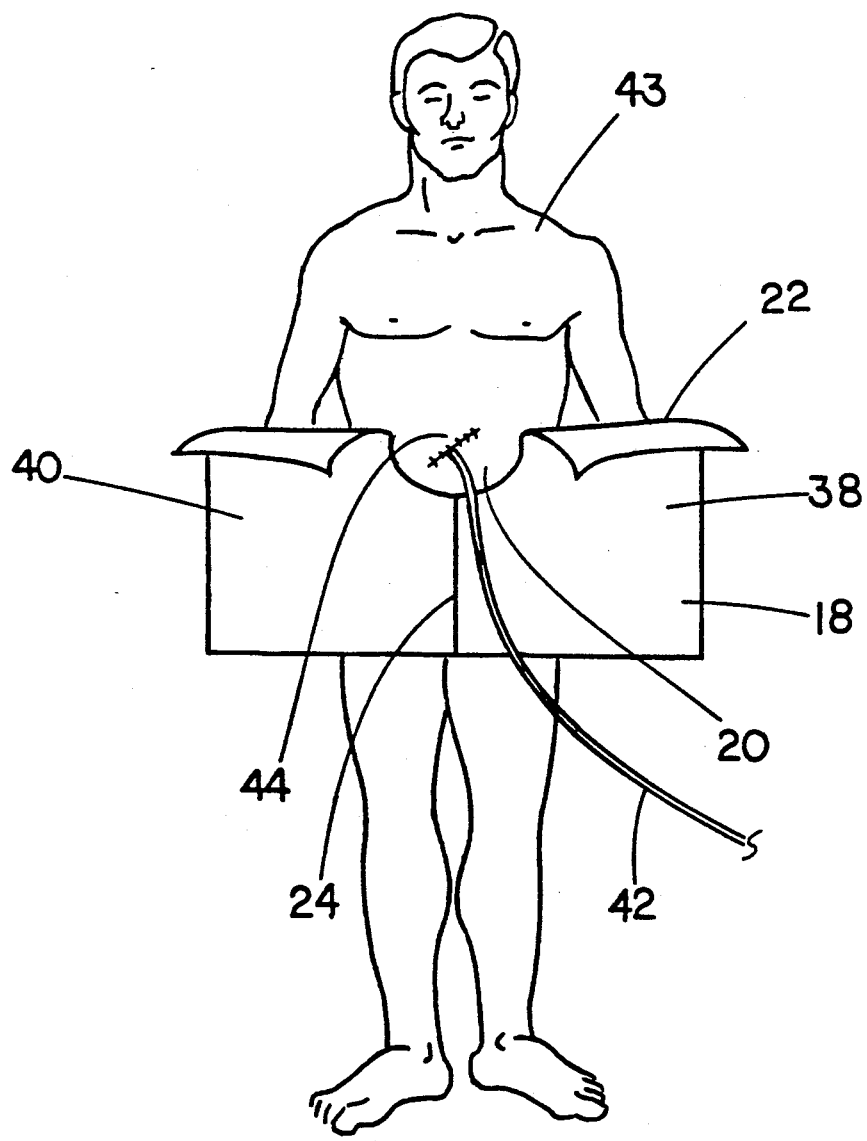
FIG. 6 is a plan view of the drape of FIG. 3 showing the use of the drape with a patient after the drape has been severed along one of its score lines.

Also as shown in FIG. 6, sheet 18 may be readily removed from the patient when an item such as tube 42 must be left in the procedure site 44 after the procedure has been completed without the need to use scissors. Once the two halves 38 and 40 have been severed at least along score line 22, the sheet may be slipped off the patient. It is also possible to sever the remainder of the sheet along score line 24 to make it even easier to remove the sheet from the patient 43 in the same fashion as the sheet was severed along score line 22.

The above-described surgical drape may be used as set forth below. After the site of the surgical procedure on patient 43 has been properly scrubbed, shaved and disinfected, release paper 34 is removed from adhesive 32. Sheet 18 is then placed on the patient with the adhesive 32 contacting the patient and with the site of the surgical procedure 44 being somewhat centered within opening 20 of the sheet. The adhesive holds the sheet in position during the procedure. The surgeon then completes the procedure.

In many cases tube 42 will remain in the site of the procedure 44 for purposes of drainage or adding fluids. In order to remove the drape, the nurse or physician grips both sides 38 and 40 of sheet 18 and quickly pulls the sides 38 and 44 away from one another, thereby severing the sheet along score line 22. The sheet then may be removed from the patient without disturbing the site of the procedure or the tube 42.

Alternatively, the surgeon or nurse may also sever the sheet along score line 24 by also pulling the two halves 38 and 44 away from each other so that the sheet 18 will become completely severed forming two separate halves which is even more easy to remove from the patient.

The above-described drape may be manufacturing as set forth below. A rectangular sheet of material is provided which is substantially impervious to microorganisms. The sheet may be made of plastic material such as, for example, polyethylene. An opening is formed in the sheet, which is preferably round, at or near the center of the sheet. The sheet is scored by a knife to a depth which is less than the full thickness of the sheet, preferably 35 percent of the entire thickness of the sheet thereby resulting in score lines form edge 26 of the sheet to edge 28 of opening 20 and edge 30 of the sheet also to edge 28 of opening 20. An adhesive in the form of a double sided tape is completely severed as indicated by slit 36. Release paper covers one side of the adhesive, however the release paper is not severed so that a rectangular release paper/adhesive may be applied to the drape. An opening is formed in the release paper/adhesive which is the same shape and size as opening 20 of the drape. The adhesive release paper is applied to the drape about opening 20 with the slit 356 aligning with portions of score liens 22 and 24 of the drape. The drape is then folded, placed into a container, and sterilized.

Thus there is provided a unique surgical drape which provides a reliable sterile field and can readily be pulled apart after the procedure has been completed so that the drape may be easily removed from the patient, particularly in situations where a tube or other elongated apparatus such as wires are left in the site of the surgical procedure after the procedure has been completed.

From the foregoing description of the preferred embodiment of the invention, it will be apparent many modifications may be made therein without departing from the true spirit and scope of the invention.

I claim:

1. A surgical drape comprising:
    a sheet of material which is substantially impervious to microorganisms; said sheet having a predetermined thickness; said sheet having an opening therein; said sheet adapted to be placed over a portion of the patient for providing a substantially sterile field during a surgical procedure; said opening adapted to be adjacent to the site of the surgical procedure;
    at least one score line located between one edge of said sheet and said opening; said score line penetrating said sheet to a depth less than the entire thickness of said sheet thereby maintaining the sterile field along said score line, whereby said sheet may be readily severed along said score line, whereby said sheet may be readily severed along said score line after the completion of the surgical procedure.

2. A surgical drape as set forth in claim 1 wherein said score line is in the form of an elongated continuous notch in said sheet.

3. A surgical drape as set forth in claim 1 wherein said score line extends to a depth of between 35% and 50% of the total thickness of said sheet.

4. A surgical drape as set forth in claim 1 further including a second score line extending from another edge of said sheet to said opening.

5. A surgical drape as set forth in claim 1 further including an adhesive material on a portion of one side of said sheet surrounding said opening.

6. A surgical drape as set forth in claim 5 wherein said adhesive material is a layer of two sided tape.

7. A surgical drape as set forth in claim 5 wherein said adhesive material is severed adjacent to said score line.

8. A surgical drape as set forth in claim 5 further including release paper attached to said adhesive material whereby said adhesive material will only be exposed at the time that said drape is to be used.

9. An apparatus as set forth in claim 1 wherein said material which is substantially impervious to microorganisms is a plastic.

10. A method for providing a sterile field for a surgical procedure comprising the steps of:
    providing a surgical drape have a fenestration therein and having a score line from at lest one edge of said drape to said fenestration; said sheet having a predetermined thickness; said score line penetrating said sheet to a depth less than the entire thickness of said sheet thereby maintaining the sterile field along said score line;
    laying said drape on said patient;
    performing a surgical procedure through said fenestration;
    inserting an elongated apparatus through said fenestration and into the site of the surgical procedure;
    completing the surgical procedure through said fenestration;
    severing said drape along said score line; and
    removing said drape from the patient.

11. A method as set forth in claim 10, wherein said drape has an adhesive about said opening and further including the step of aligning said fenestration about the site of the surgical procedure and contacting the patient with the adhesive.

12. A method for manufacturing a surgical drape comprising:

forming a sheet of material which is substantially impervious to microorganisms;

forming an opening in said sheet through which a surgical procedure is to be performed;

scoring said sheet from at least one edge to said opening to a depth in the sheet less than the full thickness of said sheet; and providing an adhesive on said sheet in the vicinity of said opening.

13. A method for providing a surgical drape as set forth in claim 12 further including the steps of:

severing said adhesive thereby forming a slit therein; said slit in said adhesive substantially aligning with said score line.

14. A method as set forth in claim 13 further comprising the steps of:

applying a release paper to said adhesive.

* * * * *